US007402611B1

(12) United States Patent
Ribes et al.

(10) Patent No.: US 7,402,611 B1
(45) Date of Patent: Jul. 22, 2008

(54) USE OF AMINO ACIDS FOR MAKING MEDICINES FOR TREATING TO INSULIN-RESISTANCE

(75) Inventors: Gérard Ribes, Montpellier (FR); Mohammed Taouis, Tours (FR); Roger Pierre Petit, Montpellier (FR); Christophe Broca, Montpellier (FR); Yves Sauvaire, Montferrier Sur Lez (FR)

(73) Assignee: Innodia Inc., Quebec (CA)

( * ) Notice: Subject to any disclaimer, the term of this patent is extended or adjusted under 35 U.S.C. 154(b) by 895 days.

(21) Appl. No.: 10/069,574

(22) PCT Filed: Aug. 23, 2000

(86) PCT No.: PCT/FR00/02361

§ 371 (c)(1),
(2), (4) Date: Aug. 1, 2002

(87) PCT Pub. No.: WO01/15689

PCT Pub. Date: Mar. 8, 2001

(30) Foreign Application Priority Data

Aug. 27, 1999 (FR) .................................. 99 10874

(51) Int. Cl.
*A61K 31/198* (2006.01)
*A61K 31/205* (2006.01)
(52) U.S. Cl. ...................................... 514/561; 514/556
(58) Field of Classification Search ...................... 514/3, 514/561
See application file for complete search history.

(56) References Cited

U.S. PATENT DOCUMENTS

| 4,529,589 | A | * | 7/1985 | Davydov et al. ............. 424/468 |
| 5,178,867 | A | * | 1/1993 | Guittard et al. .............. 424/473 |
| 5,470,879 | A | * | 11/1995 | Sauvaire et al. .............. 514/561 |
| 5,591,709 | A | | 1/1997 | Lindenbaum |
| 5,847,109 | A | | 12/1998 | Garti et al. |
| 5,997,877 | A | | 12/1999 | Chang |

FOREIGN PATENT DOCUMENTS

| FR | 2695317 | A | 3/1994 |
| FR | 2745718 | A | 9/1997 |
| WO | 9618313 | A | 6/1996 |
| WO | 9821592 | A | 5/1998 |
| WO | 9832017 | A | 7/1998 |

OTHER PUBLICATIONS

Windholz et al., The Merck Index, Tenth Edition (1983), pp. 723-724, abstract No. 4866.*
Yves Sauvaire et al., "4-hydroxyisoleucine: A Novel Amino Acid Potentiator of Insulin Secretion", Diabetes, (Feb. 1998) 47(2), pp. 206-210.*
Broca, C. et al;"Intracellular Signalling and 4-Hydroxyisoleucine Insulinotropic Effect"; Diabetologia; Aug. 1999, vol. 42, No. Suppl. 1, p. A129, XP000910386.
Broca, C. et al.; "4-Hydroxyisoleucine: Experimental Evidenced of its Insulinotropic and Antidiabetic Properties"; American Journal of Physiology; Oct. 1999, vol. 277, No. 4 Part 1, p. E617-E623; XP000908984.
Broca, C. et al; "4-Hydroxyisoleucine Improves Glucose Tolerance in Normal and NIDDIM Animals"; Biabetologia, Aug. 1998, vol. 41, No. Suppl. 1, p. A239, XP00090899.
Ricort JM et al; "Alterations in Insulin Signalling Pathway Induced by Prolonged Insulin Treatment of 3T3-L1 Adipocytes"; Diabetologia, Oct. 1995, 38, 1148-56, XP000909007.
Withers DJ et al;. "Disruption of IRS-2 Causes Type 2 Diabetes in Mice"; Nature, GB, Macmillan Journals Ltd., London, vol. 391, No. 6670, Feb. 26, 1998, pp. 900-904, XP002119312.
Publication , G.Slama; "Doibetes: Classification Et Generalities"; pp. 1453-1458.
Search Report from European Patent Application No. EP 03 29 1523, Mar. 17, 2004.
Alcock et al., "Stereochemistry of 4-Hydroxyisoleucine From Trigonella Foenum-Graecum," Phytochemistry 28:1835-1841, 1989.
Bordia et al., "Effect of Ginger (Zingiber Officinale Rosc.) and Fenugreek (Trigonella Foenumgraeum L.) on Blood Lipids, Blood Sugar and Platelet Aggregation in Patients with Coronary Artery Disease," Prostaglandins, Leukotrienes and Essential Fatty Acids 56:379-387, 1997.
Broca et al., "4-Hydroxyisoleucine: Effects of Synthetic and Natural Analogues on Insulin Secretion," Eur. J. Pharmacol. 390:339-345, 2000.
Fowden et al., "4-Hydroxyisoleucine from Seed of Trigonella Foenum-Graecum," Phytochemistry 12:1707-1711, 1973.
Khosla et al., "Effect of Trigonella Foenum-Graecum (Fenugreek) on Blood Glucose in Normal and Diabetic Rats," Indian J. Physiol. Pharmacol. 39:173-174, 1995.
Madar et al., "Glucose Lowering Effect of Fenugreek in Non-insulin Dependent Diabetics," Eur. J. Clinical Nutrition 42:51-54, 1988.

(Continued)

*Primary Examiner*—Brian-Yong S Kwon
(74) *Attorney, Agent, or Firm*—Clark & Elbing LLP (57) ABSTRACT

The invention concerns the use of monohydroxy or polyhydroxy amino acids, and the lactone forms thereof for making medicines with insulin-analogue and/or insulin-sensitizing effects on peripheral tissues targeted by insulin, and more particularly the use thereof for making medicines for treating and preventing insulin-resistance.

14 Claims, 11 Drawing Sheets

OTHER PUBLICATIONS

Neeraja et al., "Hypoglycemic Effect of Processed Fenugreek Seeds in Humans," J. Food Sci. Technol. 33:427-430, 1996.

Ohnuma et al., "Anaphylaxis to Curry Powder," Allergy 53:452-454, 1998.

Patil et al., "Allergy to Fenugreek (Trigonella Foenum Graecum)," Ann. Allergy Asthma Immunol. 78:297-300, 1997.

Petit et al., "Steroid Saponins from Fenugreek Seeds: Extraction, Purification and Pharmacological Investigation on Feeding Behavior and Plasma Cholesterol," Steroids 60:674-680, 1995.

Petit et al., "Effects of a Fenugreek Seed Extract on Feeding Behavior in the Rat; Metabolic-Endocrine Correlates," Pharmacol. Biochem. Behav. 45:369-374, 1993.

Prasanna, "Hypolipidemic Effect Fenugreek: a Clinical Study," Indian J. Pharmacol. 32:34-36, 2000.

Ribes et al., "Antidiabetic Effects of Subfractions from Fenugreek Seeds in Diabetic Dogs," Proc. Soc. Exp. Biol. Med. 182:159-166, 1986.

Ribes et al., "Effect of Fenugreek Seeds on Endocrine Pancreatic Secretions in Dogs," Ann. Nutr. Metab. 28:37-43, 1984.

Ribes et al., "Hypocholesterolaemic and Hypotriglyceridaemic Effects of Subfractions from Fenugreek Seeds in Alloxan Diabetic Dogs," Phytotherapy Res. 1:38-43, 1987.

Sauvaire et al., "Implication of Steroid Saponins and Sapogenins in the Hypocholesterolemic Effect of Fenugreek," Lipids 26:191-197, 1991.

Sauvaire et al, "Changes in Growth, Proteins and Free Amino Acids of Developing Seed and Pod of Fenugreek," Phytochem. 23:479-486, 1984.

Sauvaire et al., "Chemistry and Pharmacology of Fenugreek," *Herbs, Botanicals & Teas* Eds. G. Mazza and B.D. Oomah, 107-129, 2000.

Sharma, "Effect of Fenugreek Seeds and Leaves on Blood Glucose and Serum Insulin Responses in Human Subjects," Nutritions Res. 6:1353-1364, 1986.

Sharma et al., "Hypoglycaemic Effect of Fenugreek Seeds in Non-Insulin Dependent Diabetic Subjects," Nutrition Res. 10:731-739, 1990.

Sharma et al., "Use of Fenugreek Seed Powder in the Management of Non-Insulin Dependent Diabetes Mellitus," Nutr. Res. 16:1331-1339, 1996.

Sharma et al., "Effect of Fenugreek Seeds on Blood Glucose and Serum Lipids in Type I Diabetes," Eur. J. Clin. Nutr. 44:301-306, 1990.

Sowmya et al., "Hypocholesterolemic Effect of Germinated Fenugreek Seeds in Human Subjects," Plant Foods Hum. Nutr. 53:359-365, 1999.

Valette et al., "Hypocholesterolaemic Effect of Fenugreek Seeds in Dogs," Atherosclerosis 50:105-111, 1984.

Al-Habori et al, "Antidiabetic and Hypocholesterolaemic Effects of Fenugreek," Phytother. Res. 12:233-242, 1998.

Broca et al., "4-Hydroxyisoleucine: Experimental Evidence of its Insulinotropic and Antidiabetic Properties," Am. J. Physiol. 277:E617-E623, 1999.

Sauvaire et al., "4-Hydroxyisoleucine A Novel Amino Acid Potentiator of Insulin Secretion," Diabetes 47:206-210, 1998.

Alzaid, "Insulin Resistance in Non-Insulin-Dependent Diabetes Mellitus," Acta Diabetol. 33:87-99, 1996.

Amer et al., "Different Aetiologies of Type 2 (Non-Insulin-Dependent) Diabetes Mellitus in Obese and Non-Obese Subjects," Diabetologia 34:483-487, 1991.

Banerji et al., "Does Intra-Abdominal Adipose Tissue in Black Men Determine Whether NIDDM is Insulin-Resistant or Insulin-Sensitive?" Diabetes 44:141-146, 1995.

Bonora et al., "In Vivo Glucose Metabolism in Obese and Type II Diabetic Subjects With or Without Hypertension," 42:764-772, 1993.

Byrne et al., "Elevated Plasma Glucose 2 h Postchallenge Predicts Defects in $\beta$-Cell Function," Am. J. Physiol. 270:E572-E579, 1996.

Campbell et al., "Quantification of the Relative Impairment in Actions of Insulin on Hepatic Glucose Production and Peripheral Glucose Uptake in Non-Insulin-Dependent Diabetes Mellitus," Metabolism 37:15-21, 1988.

Gerich, "Insulin Resistance is Not Necessarily an Essential Component of Type 2 Diabetes," J. Clin. Endocrinol. Metab. 85:2113-2115, 2000.

Gerich, "The Genetic Basis of Type 2 Diabetes Mellitus: Impaired Insulin Secretion Versus Impaired Insulin Sensitivity," Endocrine Rev. 19:491-503, 1998.

Groop et al., "Insulin Resistance, Hypertension and Microalbuminuria in Patients with Type 2 (Non-Insulin-Dependent) Diabetes Mellitus," Diabetologia 36:642-647, 1993.

Groop et al., "Insulin Resistance and Insulin Deficiency in the Pathogenesis of Type 2 (Non-Insulin-Dependent) Diabetes Mellitus: Errors of Metabolism or of Methods?" Diabetologia 36:1326-1331, 1993.

Haffner et al., "Insulin Sensitivity and Acute Insulin Response in African-Americans, Non-Hispanic Whites, and Hispanics with NIDDM," Diabetes 46:63-69, 1997.

Kalant et al., "Insulin Responsiveness of Superficial Forearm Tissues in Type 2 (Non-Insulin Dependent) Diabetes," Diabetologia 22:239-244, 1982.

Nesher et al., "Insulin Deficiency and Insulin Resistance in Type 2 (Non-Insulin-Dependent) Diabetes: Quantitative Contributions of Pancreatic and Peripheral Responses to Glucose Homeostasis," Eur. J. Clin. Invest. 17:266-274, 1987.

Nosadini et al., "Impaired Insulin-Induced Glucose Uptake by Extrahepatic Tissue is Hallmark of NIDDM Patients Who Have or Will Develop Hypertension and Microalbuminuria," Diabetes 43:491-499, 1994.

O'Rahilly et al., "Beta-Cell Dysfunction, Rather than Insulin Insensitivity, is the Primary Defect in Familial Type 2 Diabetes," Lancet 2:360-364, 1986.

Pigon et al., "Normal Hepatic Insulin Sensitivity in Lean, Mild Noninsulin-Dependent Diabetic Patients," J. Clin. Endocrinol. Metab. 81:3702-3708, 1996.

Strutton et al., "Estimated Coronary Heart Disease Attributable to Insulin Resistance in Populations With and Without Type 2 Diabetes Mellitus," Am. J. Manag. Care 7:765-773, 2001.

Taniguchi et al., "Insulin Sensitivity, Insulin Secretion, and Glucose Effectiveness in Obese Subjects; a Minimal Model Analysis," Metabolism 44:1397-1400, 1995.

\* cited by examiner

Figure 11 pNPP : p-nitrophenyl phosphate

USE OF AMINO ACIDS FOR MAKING MEDICINES FOR TREATING TO INSULIN-RESISTANCE

This application is the US national phase of international application PCT/FR00/02361 filed 23 Aug. 2000, which designated the US.

The present application relates to the use of amino acids for the manufacture of medicaments with an insulin mimetic and/or insulin-sensitizing effects on the peripheral target tissues of insulin, and more particularly the use of amino acids for the manufacture of medicaments intended for the treatment and the prevention of insulin resistance.

Figure 1:
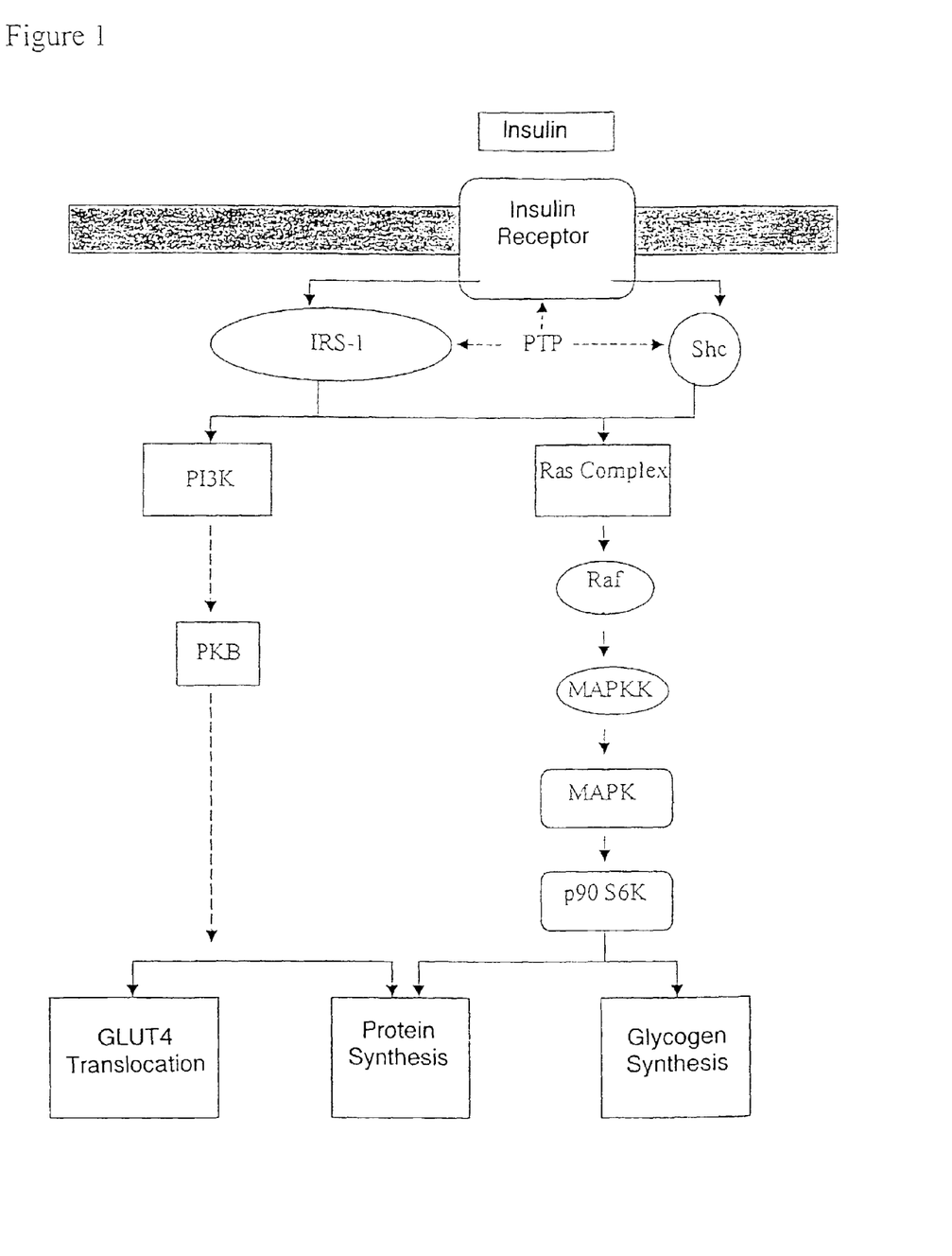

In the last few years, considerable progress has been made in the understanding of the molecular mechanisms of how insulin works. A diagram showing the main routes of transduction of the insulin signal is given in FIG. 1. The insulin receptor is a transmembrane receptor endowed with an intrinsic tyrosine kinase activity (Combettes-Souverain M. and Issad T., Diab. Metab., 24, 477, 1998). The bonding of insulin to its receptor leads to the autophosphorylation of the receptor on its tyrosine residues, which stimulates its tyrosine kinase activity towards a certain number of intracellular substrates such as Insulin Receptor Substrate 1 (IRS-1), Insulin Receptor Substrate 2 (IRS-2) and Src homology collagen protein or Shc. This tyrosine kinase activity plays a determining role in the transmission of the insulin signal, and it is altered in numerous situations of insulin resistance (Ricort J. M. et al., Diabetologia, 38, 1148, 1995). Overall the cellular mechanisms of insulin resistance can be found at the bonding of the hormone to its receptor or a more distal post-bonding stage to the receptor. As the diagram in FIG. 1 shows, the phosphorylation on the tyrosines of IRS and Shc by the insulin receptor allows the activation of two main routes of cellular signalling, the MAP kinase (MAPK) route and the phosphatidylinositol 3-kinase (PI 3-K) route. Phosphotyrosine phosphatase (PTP) plays a role in the regulation of these routes.

The inventors have previously reported the insulin secretor effect that can be exercised in pancreatic cells by hydroxylated amino acid extracts of fenugreek seeds (*Trigonella foenum graecum* L.), and in particular by 4-hydroxyisoleucine (4-OH-Ile) and/or the corresponding lactone (Patents FR 2 695 317 and 2 745 718 and corresponding patents under priority).

Moreover the inventors have now shown that such compounds are also able to act at the level of the insulin target cells, namely the peripheral tissues such as the liver and muscle, by exercising an activity at the level of the insulin receptor and/or the cascade of signalling that the activation of this receptor triggers. The effect observed in these peripheral tissues corresponds overall to an insulin mimetic or insulin-sensitizing effect.

The work carried out, as illustrated by the examples, has in fact shown the effect of these compounds at the level of the phosphorylation cascade set in motion under the receptor, notably the increase of phosphorylation of the main proteins involved in the transmission of the insulin signal. The PI 3-kinase (Phosphatidylinositol 3-kinase) enzyme activated by phosphorylated IRS-1 and playing an essential role in the translocation of the glucose transporter GLUT 4, is also increased under the effect of such compounds. Under the same conditions of use of these compounds, the phosphatase activity associated with the signalling route of the insulin receptor (PTP activity) is lowered, which is consistent with the increase of phosphorylations mentioned above. These compounds are therefore capable of acting on the signalling routes which are normally triggered by insulin, whether it is by activation of kinases, and/or inhibition of phophatases.

A subject of the present invention is to benefit from the results obtained, and thus relates to any use of such amino acids or their derivatives, as insulin mimetic or insulin-sensitizing agents. It in particular relates to any use of such compounds for the manufacture of medicaments with insulin mimetic and/or insulin-sensitizing effects. These effects can be observed in the peripheral target tissues of insulin. As these compounds act on the signalling routes which are normally triggered by insulin, they can in fact serve as substitutes, complements, potentializers and sensitizers to insulin.

The present application thus relates to the use as an insulin mimetic or insulin-sensitizing agent, of any amino acid or amino acid derivative which exercises a reduction in the phosphatase PTP activity and/or an increase of PI 3-kinase activity, of an equivalent or even higher level to the reduction, or increase respectively, caused by insulin. Any means which makes it possible to note such an effect on the reduction in PTP activity or increase in PI 3-kinase activity is appropriate. The following examples give illustrations.

Such compounds correspond in a remarkable manner to amino acids which do not recognise the insulin receptor on its binding site, but which act at the post receptor level, under the conditions mentioned in the examples for 4-OH-Ile, and also correspond to the derivatives of these amino acids which have retained, at least in kind, the properties of non-recognition of the insulin receptor on its binding site and activity at post-receptor level that the parent amino acid of said derivative presents.

Advantageously, the use according to the invention is characterised in that it relates to a compound chosen from the group constituted by mono-hydroxylated amino acids, poly-hydroxylated amino acids, and lactonic forms of these mono- or hydroxylated amino acids.

In particular the invention relates to the use of 4-hydroxyisoleucine of formula and/or its lactonic form.

In particular, the invention relates to the use of 4-hydroxyisoleucine (abbreviated to 4-OH-Ile) in the form of its 2S, 3R, 4S isomer, or the corresponding lactone.

Taking into account the effects observed, the medicaments manufactured in accordance with the invention are particularly suitable for treating insulin resistance, for combating or preventing syndromes linked to insulin resistance, and for preventing insulin resistance.

Moreover, it is known that excessive weight gain, lack of exercise, poor diet and the ever increasing number of elderly people are socio-economic factors frequently encountered in western countries. All contribute to the development of insulin resistance and compensatory hyperinsulinemia often combined with obesity and are potentially diabetogenic. Thus, the free fatty acids are amongst the first candidates put forward to attempt to explain the close relationship between insulin resistance, obesity and hyperinsulinism (Mac Garry J. D., J. Cell. Biochem., 555, 29, 1994).

Today this relationship has become a major phenomenon as regards public health. A body of proof, both clinical and epidemiological, linking hyperinsulinemia to the risk of future cardiovascular diseases, athergenic or diabetogenic risk, has made it possible to draw up the consistent Reaven's X syndrome table (hyperinsulinemia, insulin resistance, increase of serum triglycerides, arterial hypertension) and the morbid risks which are associated with it (Reaven G. M., Diabetes, 37, 1595, 1988). In addition, according to recent investigations, hyperinsulinemia by encouraging the proliferation of certain epithelial cells (notably those in the colon) appear to be associated with the risk of cancer (Hu F. B. et al., J. Natl. Cancer Inst., 91, 542, 1999).

The present application also relates to any use of said amino acids and derivatives for the manufacture of a medicament intended to combat insulin resistance and insulin resistance syndromes, in particular against hyperinsulinemia, insulin resistance linked to ageing and against illnesses linked with obesity.

The present application also relates to any use of said amino acids and derivatives for the manufacture of a medicament intended to prevent insulin resistances, and in particular for the manufacture of a medicament intended to reduce the need for exogenic insulin. Such medicaments, because of their insulin mimetic and insulin-sensitizing properties, can in fact have the effect of reducing the need for exogenic insulin that patients whose endogenic insulin is deficient, even absent in the case of type 1 diabetes present. Patients suffering from type 1 diabetes suffer in fact from a total absence of the secretion of insulin (destruction of producing cells) which restricts full exogenic supplies of insulin. This situation, besides the intrinsic cost of such administration, often leads to the development of insulin resistance. In order to prevent and remedy these problems, for the treatment of a deficit in endogenic insulin, and in particular an absence of endogenic insulin such as type 1 diabetes, and for the manufacture of a medicament intended for such treatments, the present invention proposes to use at least one of said amino acids or derivatives. Used in combination with insulin, they have the advantage of reducing the need for exogenic insulin in the patient (reduction of the necessary supply of insulin), and therefore reduce the cost of treatment whilst preventing the development of insulin resistance and its side effects.

The medicaments manufactured in accordance with the invention could also be used to contribute to the inhibition of the proliferation of certain cell lines associated with the risk of cancer appearing.

The invention also relates to the use of said derivatives, in particular 4-hydroxyisoleucine and/or its lactonic form to manufacture medicaments which act by reducing the phosphatase activity associated with the signalling route of the insulin receptor, and/or by stimulating the PI 3-kinase activity on IRS-1 and/or IRS-2.

The present invention also relates to any pharmaceutical composition, any pharmaceutical kit and any medicament comprising, in a combined fashion, insulin and at least one of the amino acid compounds or derivatives defined above. This combination can be physical (insulin and amino acid or derivative are thus in the same composition). Or alternatively it can correspond to a presentation of insulin on one hand, and amino acid or derivative on the other hand, in physically distinct compositions, but which are presented as combined for combined use (kit-of-parts). This combined use can be simultaneous or at different times.

The medicaments according to the invention can be administered mainly by oral route, but also by intravenous or intramuscular route, and contain excipients which are chosen according to the adopted galenic form.

The dosage will be adapted according to the pathology to be treated.

Other characteristics and advantages of the invention are given, by way of illustration, in the examples which follow, in which reference is made to FIGS. 2 to 11 (FIG. 1 was referred to above and shows the diagram of the main routes of transduction of the insulin signal), these FIGS. 2 to 11 represent:

MEASUREMENT OF THE PI 3-KINASE ACTIVITY

The PI 3-kinase activity was measured on immunoprecipitates carried out with the anti-IRS-1 antibody. This made it possible to determine the enzymatic activity associated with the action of insulin and to compare it to the action induced by 4-OH-Ile.

Experimental Protocol

Normal male Wistar rats (IFFA CREDO strain, France) received, via intraperitoneal injection, either ordinary insulin on its own (100 U/kg) or 4-OH-Ile on its own (18 mg/kg), or insulin combined with 4-OH-Ile in the same doses. The control rats received sodium chloride at 9‰ via intraperitoneal route. Fifteen minutes after the injection, the animals were sacrificed and the peripheral tissues (liver, muscle) were immediately removed and frozen in liquid nitrogen.

For the determination of the PI 3-kinase activity, the tissues are ground in a buffer containing protease and phosphatase inhibitors as well as a solubilising agent (Triton), as described by Taouis et al., J. Biol. Chem., 269, 14912, 1994. After solubilisation, the supernatants are immunoprecipitated with anti-IRS-1 and the PI 3-kinase activity is measured in the immunoprecipitate. In fact, the reaction is initiated by the addition of an artificial substrate of the enzyme: phosphatidylinositol (PI) and ($^{33}$P) gamma ATP. The product of the reaction is subjected to thin layer chromatography (TLC plate) and the levels of phosphorylation of PI are measured by a STORM phospho-imager (Molecular Dynamics). The activity is expressed in arbitrary units given by the apparatus (conversion of the radioactivity to luminescence by means of a laser beam).

Measurement of the Phosphatase Activity Associated with the Insulin Signalling Route The phosphatase activity was measured on the immunoprecipitates carried out with the anti-IRS-1 antibody and insulin anti-receptor.

The solubilisation protocol is the same as that for PI 3-kinase following the methodology described by Taouis et al. (J. Biol. Chem., 269, 14912, 1994). After immunoprecipitation, the phosphatase activity was measured according to the method described by Chen. et al. (J. Biol. Chem., 272, 8026, 1997).

EXAMPLE 1

Figure 2:
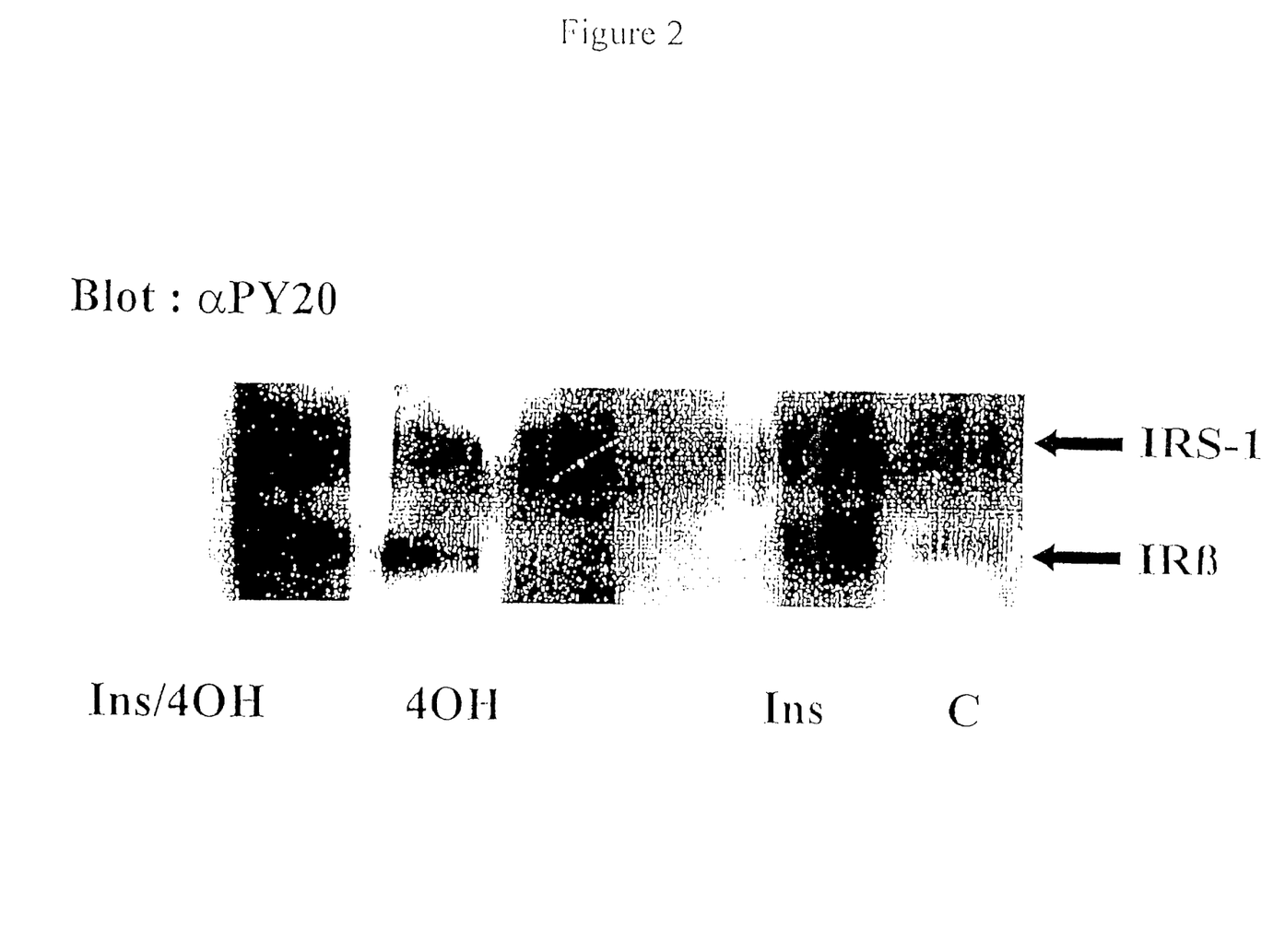
FIG. 2, the effect of 4-OH-Ile on the phosphorylation of the insulin receptor and its substrate in rat liver, FIG. 3, the effect of 4-OH-Ile on the PI 3-kinase activity of the liver, FIG. 4, the bonding of insulin on its receptor in hepatic LMH cell lines, respectively, FIGS. 5 to 11, the effect of 4-OH-Ile on,
the PI 3-kinase activity of the muscle (FIG. 5),
basal insulinemia and glycemia in rats (FIG. 6),
the PI 3-kinase activity of the liver (FIG. 7) and of the muscle (FIG. 8) in type 2 diabetic rats,
the PI 3-kinase activity of the obese Zucker rat (fa/fa) (FIG. 9),
the PI 3-kinase activity associated with the PDGF receptor or to the insulin receptor in the liver of a normal rat (FIG. 10), and
the phosphatase activity associated with IRS-1 in the liver of a normal rat (FIG. 11).

Comparison of the Effects of Insulin and 4-OH-Ile on the Phosphorylation of the Insulin Receptor and IRS-1 in the Liver of Normal Rats The results in FIG. 2 clearly show that the treatment of animals by a single injection of 4-OH-Ile (200 µg/kg I.P.) induces the activation of the insulin receptor (IR) and its substrate (IRS-1) in vivo. The effect of 4-OH-Ile (4OH) is comparable to that of insulin (Ins).

These results show the insulin mimetic effects of 4-OH-Ile in the activation of the phosphorylation of the insulin receptor and IRS-1 the phosphorylation of which is indispensable for the activation of effector proteins such as PI 3-kinase.

EXAMPLE 2

Figure 3:
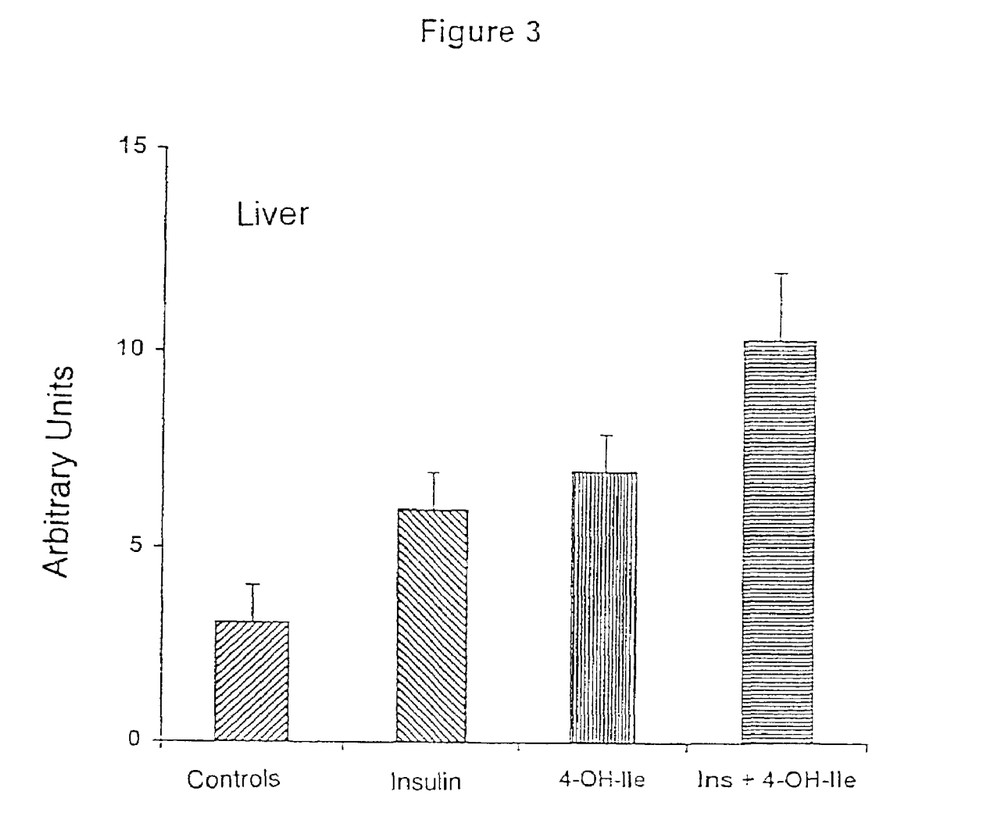

Comparison of the Effects of Insulin and 4-OH-Ile on the PI 3-Kinase Activity of the Liver The results in histograms are given in FIG. 3. In this diagram, it can be seen that insulin but also 4-OH-Ile on their own, significantly stimulate ($p<0.05$) the hepatic PI 3-kinase activity. When the two substances are administered together, a much greater effect is apparent.

These observations demonstrate that 4-OH-Ile has insulin mimetic effects in the liver. In addition, the greater effect objectivized when the two substances are injected jointly encourages synergetic activation mechanisms.

This is confirmed by the comparative study of the effects of insulin and 4-hydroxyisoleucine on the insulin membrane receptor of the hepatocyte: the 4-hydroxyisoleucine has no bond with this receptor.

Figure 4:
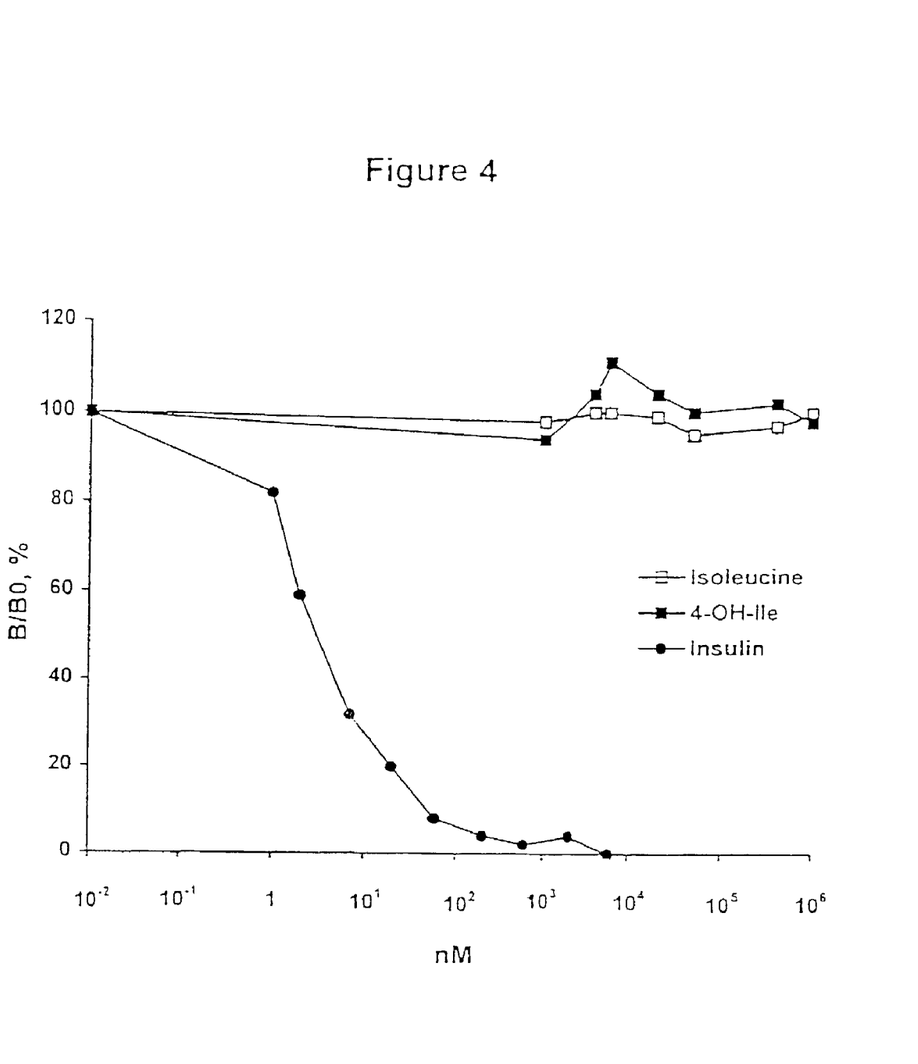

In FIG. 4 the comparative results concerning the bonding of isoleucine and 4-OH-Ile are given. The LMH cells used in these trials are from chicken hepatocarcinoma (Kawaguchi T. et al., Cancer Res., 47, 4460, 1987).

EXAMPLE 3

Figure 5:
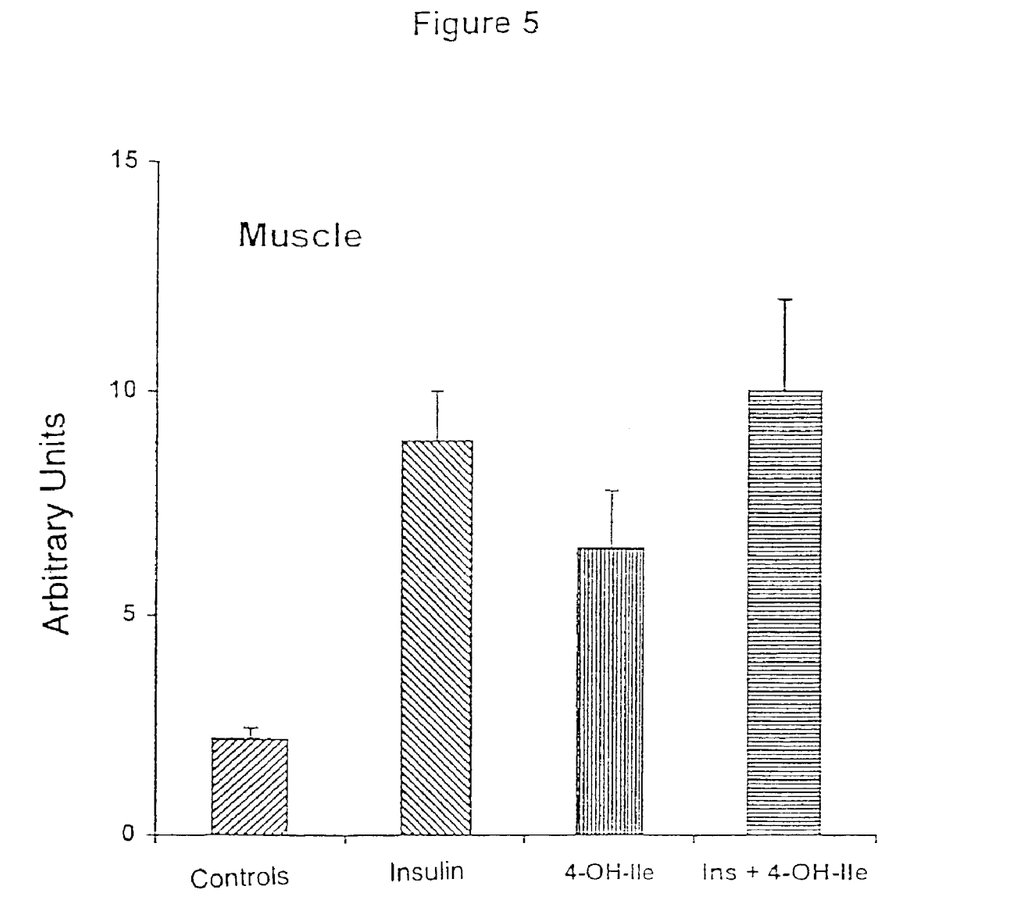

Comparison of the Effects of Insulin and 4-OH-Ile on the PI 3-Kinase Activity of Muscle The results in histograms are shown in FIG. 5. In this diagram, it can be noted that not only insulin clearly stimulates the PI 3-kinase activity, but also that 4-OH-Ile has a comparable effect. Thus, the insulin mimetic effects of 4OH-Ile observed at hepatic level are confirmed at muscular level.

It is noted therefore in the examination of the results of Examples 1 and 2 that at liver and muscle level, 4-hydroxyisoleucine stimulates, independently from insulin, the IRS-1/PI 3-kinase route which is the major route in the control of metabolic and mitogenic actions of insulin. In addition, 4-hydroxyisoleucine does not recognise the insulin receptor, or at least does not enter into competition with insulin in binding to the receptor.

EXAMPLE 4

The beneficial effect of 4-hydroxyisoleucine against relative hyperinsulinemia has been researched in vivo during chronic administration (for one month) of plant amino acid (25 mg/kg/day, by intraperitoneal route) on rats made non insulin dependant diabetic (type 2 diabetes) by joint injections of nicotinamide and streptozotocin (Masiello et al., Diabetes, 47, 224, 1998). Regular blood samples are taken from the caudal vein of the rats made it possible to evaluate the level of plasmatic insulin using a radio-immunological method (Herbert et al., J. Clin. Endocr., 25. 1375, 1965), 15 hours after injection of the product which took place at 5.30 pm. In these same samples, the plasmatic glucose level was measured using an enzymatic method (Trinder P., J. Clin. Pathol. 22, 158, 1969).

Figure 6:
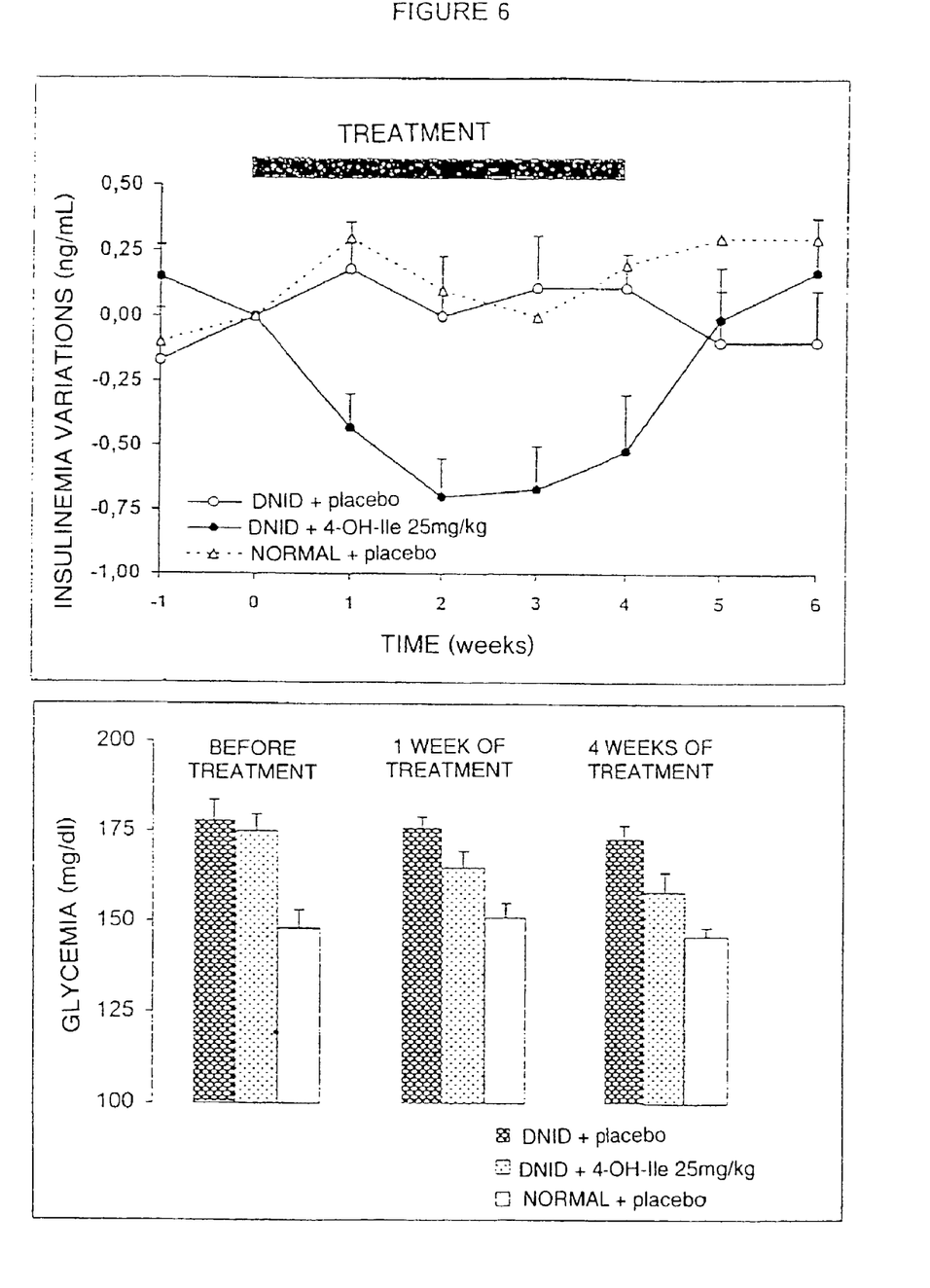

The results obtained are shown in FIG. 6.

It is observed that the daily administration of 4-hydroxyisoleucine has the effect of significantly lowering ($p>0.05$) the insulinemia of the animals treated.

In addition, after cessation of the treatment, it can be noted that the plasmatic insulin again rises to regain values close to those observed before the treatment. Under these conditions, a slight reduction in glycemia was observed at the end of the treatment.

The lowering of insulinemia observed in the rat after a chronic treatment with 4-hydroxyisoleucine confirms in vivo the insulin mimetic and/or insulin-sensitizing effects observed during experiments in vitro.

EXAMPLE 5

Comparison of the Effects of Insulin and Those of 4-OH-Ile on the PI 3-Kinase Activity of the Muscle and the Liver Removed from Rats with Type 2 Diabetes (Masiello et al., Diabetes 47, 224, 1998)

Figure 7:
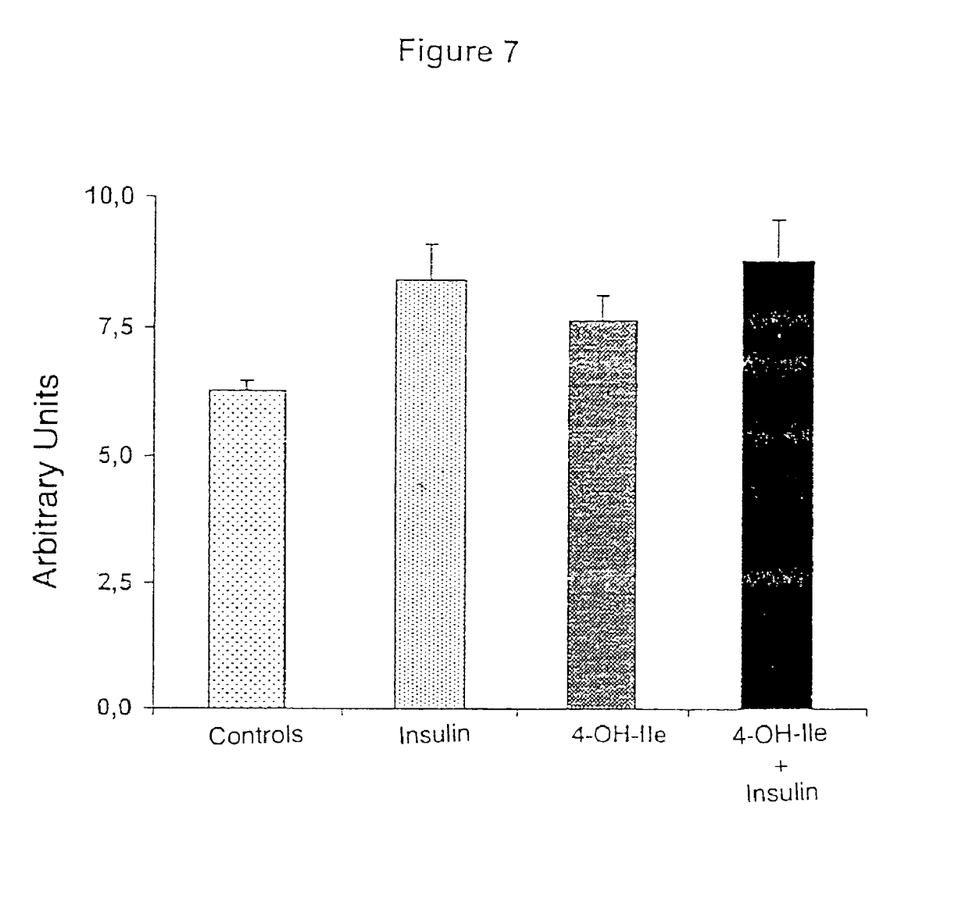
Figure 8:
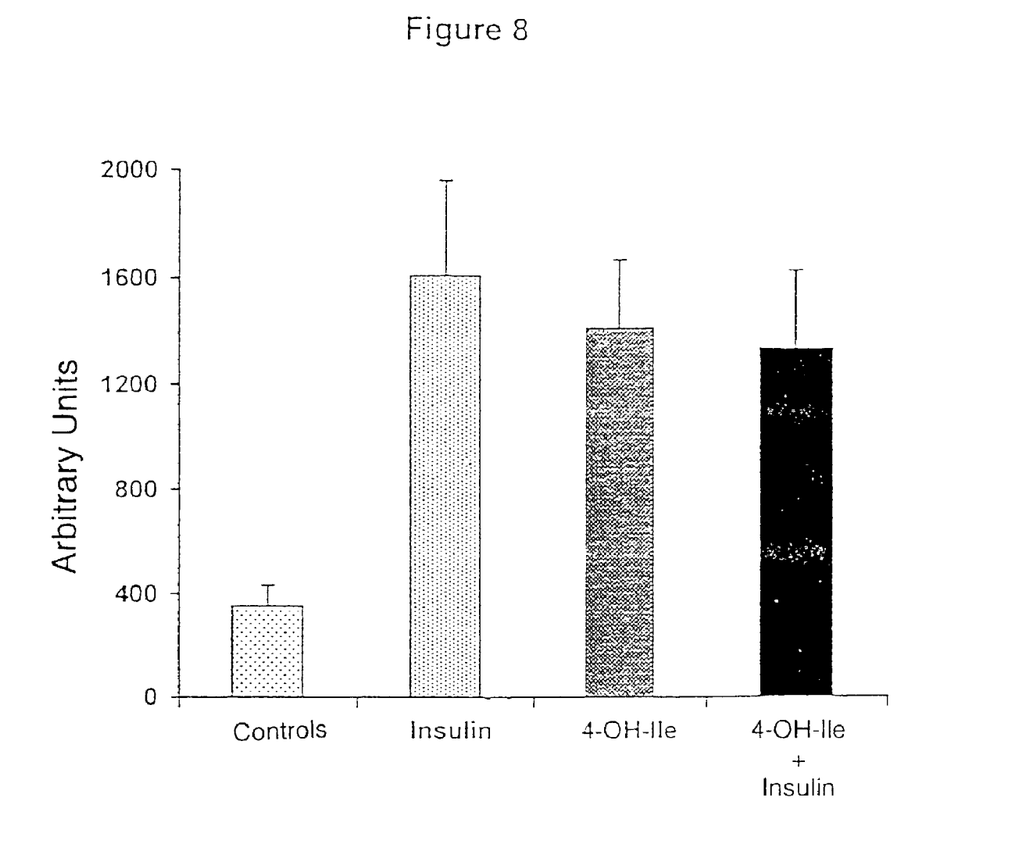

The results in histograms are shown in FIGS. 7 and 8. It is noted that, if insulin activates hepatic PI 3-kinase (FIG. 7) and muscular PI 3-kinase (FIG. 8), it is the same for the 4-OH-Ile. 4-OH-Ile in this pathological situation induces the same effect as insulin with the same intensity.

In addition, it is noticed that 4-OH-Ile significantly stimulates the IRS-1/PI 3-kinase route more clearly in the muscle ($p<0.01$) than in the liver ($p<0.05$).

EXAMPLE 6

Figure 9:
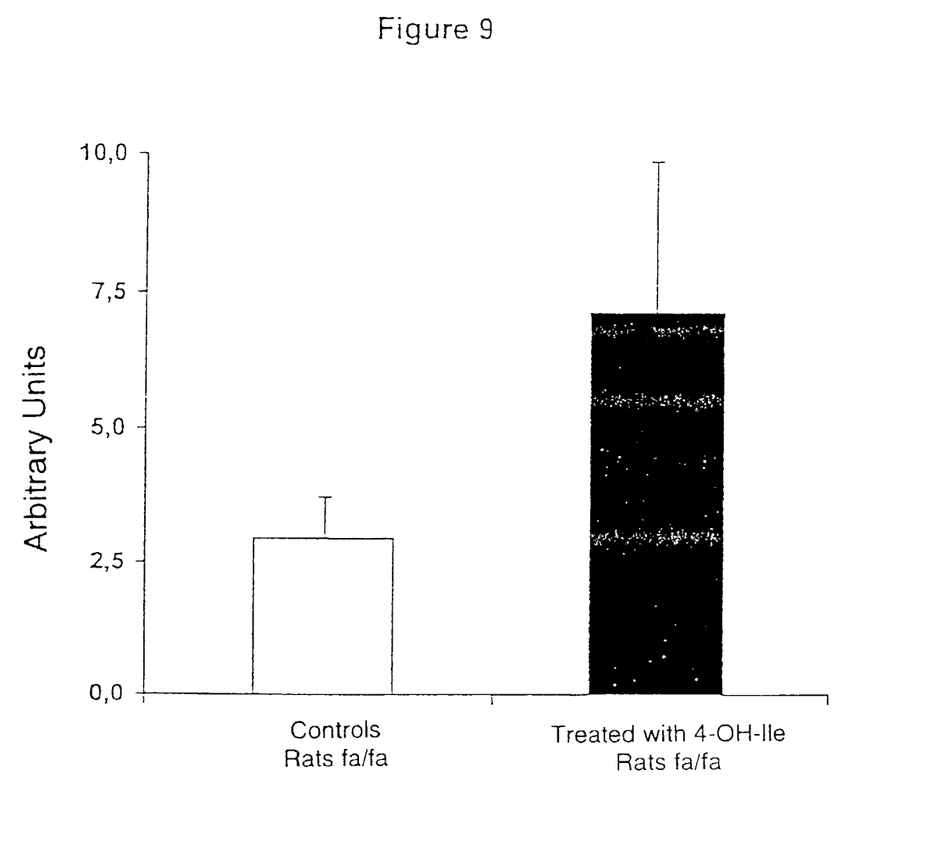

During chronic administration for 4 weeks of 4-OH-Ile (50 mg/kg by intraperitoneal route) in obese Zucker rats (fa/fa), the PI 3-kinase activity of the liver was measured at the end of the treatment. The results in histograms are shown in FIG. 9. They show that the basal activity of PI 3-kinase (animals sacrificed 17 hours after the last administration of 4-OH-Ile) is increased in the animals treated.

EXAMPLE 7

The 4-OH-Ile activates the PI 3-kinase associated with the insulin receptor but not that associated with the PDGF receptor (Platelet Derived Growth Factor).

The PI 3-kinase activities of the PDGF receptor and of the insulin receptor in the presence or the absence of 4-OH-Ile (18 mg/kg I.P.) were compared following the protocol already described.

Figure 10:
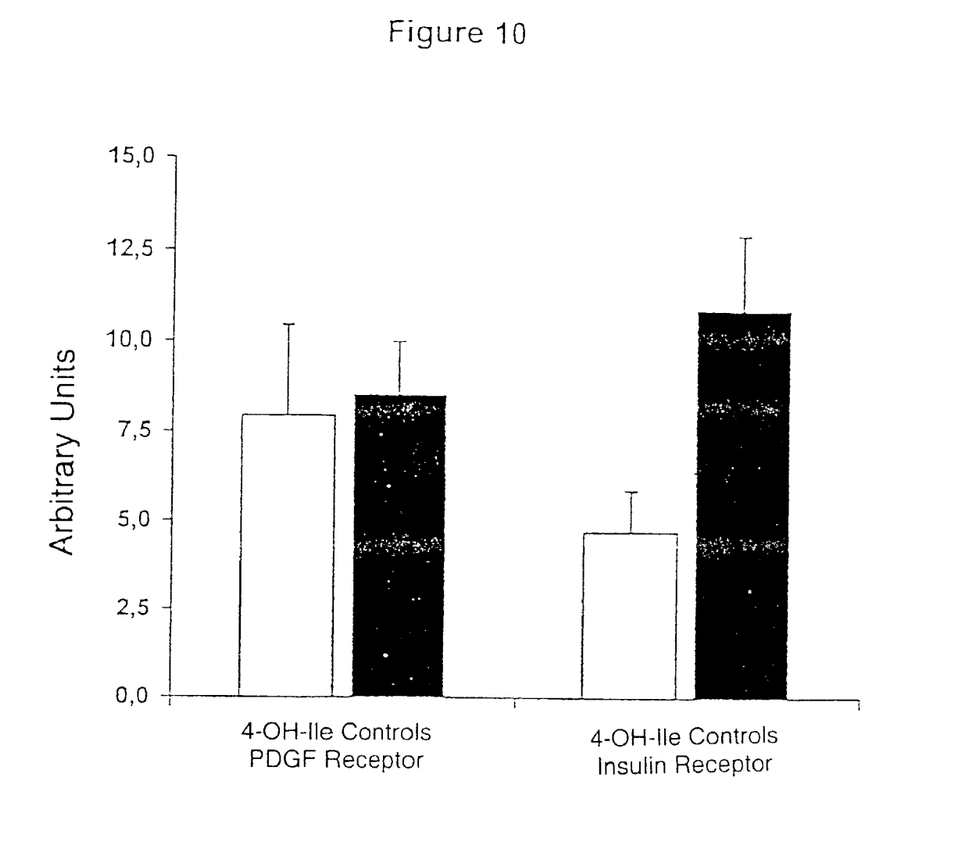

The results in histograms are shown in FIG. 10: they clearly show the specificity of the route of action of 4-OH-Ile at the level of the rat liver, that is to say that the PI 3-kinase activity associated with the insulin receptor is the only one increased ($p<0.05$).

EXAMPLE 8

Effect of 4-OH-Ile on the Phosphatase Activity Associated with the Signalling Route of the Insulin Receptor With the aim of better locating the action site of the 4-OH-Ile, its impact on phosphatase activity was studied. The phosphatase activity associated with IRS-1 was measured.

Figure 11:
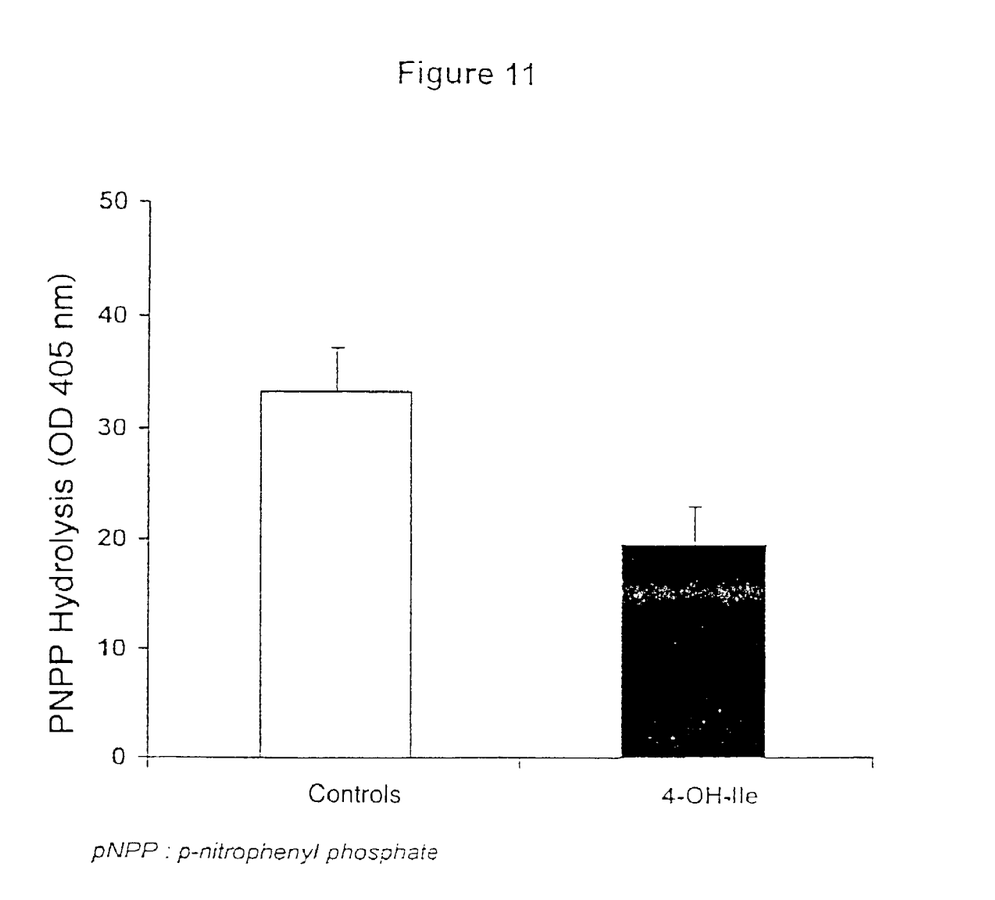

FIG. 11 shows that 4-OH-Ile (200 µmol/l) significantly inhibits (p<0.05) this activity in the liver of a normal rat.

EXAMPLE 9

A medicament according to the invention is particularly suitable for the symptomatic treatment of insulin resistant states, in particular insulin resistant states combined with obesity. It can be prepared from a mono- or polyhydroxylated amino acid and/or its lactonic forms using any appropriate technique known to a person skilled in the art. It can, in particular, be made from 4-hydroxyisoleucine. This product being hydrosoluble, such a medicament can easily be made in the form of a solution (in physiological serum for example), or in solid galenic form such as tablets or capsules. The pathologies targeted being chronic, administration by oral route appeared to be the most suitable. Such medicaments can thus be easily administered in multiple daily doses, adapted to the individual case of the patient involved, for example in the order of 2 to 3 times per day. A medicament according to the invention can also comprise insulin.

The invention claimed is:

1. A method of inducing an insulin sensitizing or insulin mimetic effect in a tissue of a patient having hyperinsulinemia, the method comprising administering to the patient 4-hydroxyisoleucine of formula and/or the lactonic form thereof.

2. The method of claim 1, wherein said 4-hydroxyisoleucine and/or lactonic form thereof exercises an insulin mimetic and/or insulin-sensitizing effect at the level of a peripheral target tissue of insulin.

3. The method of claim 1, wherein said 4-hydroxyisoleucine and/or lactonic form thereof reduces phosphatase activity associated with the signaling route of the insulin receptor, and/or stimulates phosphatidylinositol 3-kinase (PI 3-K) on insulin receptor substrate 1 (IRS-1) and/or insulin receptor substrate 2 (IRS-2).

4. The method of claim 1, wherein the 4-hydroxyisoleucine is presented in the form of its 2S, 3R, 4S isomer or the corresponding lactone.

5. The method of claim 1, wherein administration of the 4-hydroxyisoleucine and/or lactonic form thereof reduces the need of the patient for exogenic insulin.

6. A method of inducing an insulin sensitizing effect in a tissue of a patient having hyperinsulinemia, the method comprising administering to the patient 4-hydroxyisoleucine of formula and/or the lactonic form thereof.

7. A method of inducing an insulin mimetic effect in a tissue of a patient having hyperinsulinemia, the method comprising administering to the patient 4-hydroxyisoleucine of formula and/or the lactonic form thereof.

8. The method of claim 1, further comprising administering insulin to the patient.

9. The method of claim 1, wherein the 4-hydroxyisoleucine and/or lactonic form thereof is orally administered to the patient.

10. The method of claim 1, wherein the 4-hydroxyisoleucine and/or lactonic form thereof is administered to the patient two times per day.

11. The method of claim 1, wherein the 4-hydroxyisoleucine and/or lactonic form thereof is administered to the patient three times per day.

12. The method of claim 1, wherein the 4-hydroxyisoleucine and/or lactonic form thereof is administered in the form of a capsule.

13. The method of claim 1, wherein the 4-hydroxyisoleucine and/or lactonic form thereof is administered in the form of a tablet.

14. A method to combat insulin resistance in a patient having hyperinsulinemia, comprising administering to the patient the (2S, 3R, 4S) isomer of 4-hydroxyisoleucine of formula and/or the lactonic form thereof.

\* \* \* \* \*

UNITED STATES PATENT AND TRADEMARK OFFICE
CERTIFICATE OF CORRECTION

PATENT NO. : 7,402,611 B1  Page 1 of 1
APPLICATION NO. : 10/069574
DATED : July 22, 2008
INVENTOR(S) : Ribes et al.

It is certified that error appears in the above-identified patent and that said Letters Patent is hereby corrected as shown below:

Column 4, Line 40, replace "9 $\%_0$" with --9%--.

Column 5,
        Line 14, replace "in vivo" with --*in vivo*--.
        Line 52, replace "40H" with --4-OH--.
        Line 66, replace "in vivo" with --*in vivo*--.

Column 6,
        Line 22, replace "in vivo" with --*in vivo*--.
        Line 24, replace "in vitro" with --*in vitro*--.

Signed and Sealed this

Fifth Day of May, 2009

JOHN DOLL
*Acting Director of the United States Patent and Trademark Office*